US009775580B2

(12) United States Patent
Proksa et al.

(10) Patent No.: US 9,775,580 B2
(45) Date of Patent: Oct. 3, 2017

(54) CARDIAC RECONSTRUCTION FOR PHOTON COUNTING CT FOR HEART AND LUNG IMAGES

(71) Applicant: KONINKLIJKE PHILIPS N.V., Eindhoven (NL)

(72) Inventors: Roland Proksa, Neu Wulmstorf (DE); Thomas Koehler, Norderstedt (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/519,176

(22) PCT Filed: Oct. 12, 2015

(86) PCT No.: PCT/IB2015/057791
§ 371 (c)(1),
(2) Date: Apr. 14, 2017

(87) PCT Pub. No.: WO2016/063171
PCT Pub. Date: Apr. 28, 2016

(65) Prior Publication Data
US 2017/0231590 A1    Aug. 17, 2017

Related U.S. Application Data

(60) Provisional application No. 62/065,939, filed on Oct. 20, 2014.

(51) Int. Cl.
*A61B 6/03* (2006.01)
*A61B 6/00* (2006.01)

(52) U.S. Cl.
CPC ............ *A61B 6/5205* (2013.01); *A61B 6/032* (2013.01); *A61B 6/405* (2013.01); *A61B 6/4241* (2013.01);
(Continued)

(58) Field of Classification Search
CPC ......... A61B 6/03; A61B 6/032; A61B 6/4241; A61B 6/503; A61B 6/504; A61B 6/507;
(Continued)

(56) References Cited

U.S. PATENT DOCUMENTS

| 6,931,094 B2* | 8/2005 | Li .......................... A61B 6/032 378/22 |
| 9,111,337 B2* | 8/2015 | Ramirez Giraldo ...... G06T 5/50 |

(Continued)

FOREIGN PATENT DOCUMENTS

| EP | 2452626 | 5/2012 |
| JP | 2011/056167 | 3/2011 |

(Continued)

OTHER PUBLICATIONS

Koken, "Aperture weighted cardiac reconstruction for cone-beam CT," Phys. Med. Biol. 51 (2006) 3433-3448.
(Continued)

*Primary Examiner* — Thomas R Artman (57) ABSTRACT

A method includes modulating a flux of emission radiation between a first lower flux level and a second higher flux level in coordination with a cardiac cycle signal so that the flux is at the first lower flux level during a first cardiac motion phase having a first higher cardiac motion and is at the second higher flux level during a second cardiac motion phase having a second lower cardiac motion. The method further includes reconstructing the projection data with a first reconstruction window, which applies a first higher weight to a first sub-set of the projection data that corresponds to the first cardiac motion phase and the lower first flux level and a second lower weight to a second sub-set of the projection data that corresponds to the second cardiac motion phase and the higher second flux level, to generate first volumetric image data.

21 Claims, 5 Drawing Sheets

(52) U.S. Cl.
CPC ............ *A61B 6/503* (2013.01); *A61B 6/5258* (2013.01); *A61B 6/5288* (2013.01); *A61B 6/541* (2013.01)

(58) Field of Classification Search
CPC ....... A61B 6/52; A61B 6/5205; A61B 6/5235; A61B 6/5258; A61B 6/5288; A61B 6/541
See application file for complete search history.

(56) References Cited

U.S. PATENT DOCUMENTS

| | | | |
|---|---|---|---|
| 2005/0078791 A1* | 4/2005 | Li | A61B 6/032 378/95 |
| 2007/0116172 A1 | 5/2007 | Hsieh | |
| 2007/0147579 A1* | 6/2007 | De Man | A61B 6/032 378/16 |
| 2011/0075810 A1* | 3/2011 | Sendai | A61B 6/4042 378/95 |
| 2014/0105477 A1* | 4/2014 | Ramirez Giraldo | G06T 5/50 382/131 |
| 2015/0085972 A1* | 3/2015 | Choi | A61B 6/541 378/8 |
| 2016/0317102 A1* | 11/2016 | Ishii | A61B 6/035 |

FOREIGN PATENT DOCUMENTS

| | | |
|---|---|---|
| WO | 2010/070583 | 6/2010 |
| WO | 2013144812 | 10/2013 |

OTHER PUBLICATIONS

Nielsen, "Cardiac cone-beam CT volume reconstruction using ART," Med. Phys. 32 (4) (2005) 851-860.

* cited by examiner

CARDIAC RECONSTRUCTION FOR PHOTON COUNTING CT FOR HEART AND LUNG IMAGES

CROSS REFERENCE TO RELATED APPLICATIONS

This application is the U.S. National Phase application under 35 U.S.C. §371 of International Application No. PCT/IB2015/057791, filed Oct. 12, 2015, published as WO 2016/063171 on Apr. 26, 2016, which claims the benefit of U.S. Provisional Patent Application No. 62/065,939 filed Oct. 20, 2014. These applications are hereby incorporated by reference herein.

FIELD OF THE INVENTION

The following generally relates to cardiac imaging with a photon counting detector, and is described with particular application to computed tomography (CT). However, the following is also amenable to other imaging applications.

BACKGROUND OF THE INVENTION

A computed tomography (CT) scanner includes an x-ray tube that emits x-ray radiation. The radiation traverses a subject or object located in a field of view and is attenuated thereby. A detector array detects the radiation traversing the field of view and produces a signal indicative thereof. A reconstructor reconstructs the signal to produce volumetric image data.

Computed tomography scanners configured for spectral imaging have included photon counting detector pixels. With such pixels, the generated signals include electrical currents or voltages, each having a peak amplitude or a peak height that is indicative of the energy of a detected photon. The signal is energy resolved and subsequently processed. The reconstructor reconstructs spectral and non-spectral volumetric image data.

Cardiac CT requires high fluxes to get sufficient signal-to-noise-ratio during fast gantry rotation as required to virtually freeze the heart motion during the scan. With a high flux cardiac CT scan, some of the detectors will receive high flux. For example, detectors receiving radiation traversing a periphery of the patient and/or the lungs of the patient, where the patient has only small attenuation, will receive high flux.

Unfortunately, photon counting detector pixels have a limited count rate. As a consequence, a CT scanner configured with photon counting detector pixels may not be well-suited for high flux cardiac CT studies.

SUMMARY OF THE INVENTION

In one aspect, a method includes modulating a flux of emission radiation between a first flux level and a second different flux level in coordination with a cardiac cycle signal so that the flux is at the first flux level during a first cardiac motion phase having a first cardiac motion and is at the second flux level during a second cardiac motion phase having a second cardiac motion, wherein the first flux level is less than the second flux level, and wherein the first cardiac motion is greater than the second cardiac motion. The method further includes detecting the modulated emission radiation and producing projection data indicative of the detected modulated emission radiation. The method further includes reconstructing the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

In another aspect, an imaging system includes a radiation source configured to rotate about an examination region and emit radiation that traverses the examination region. A radiation source controller is configured to control the radiation source to modulate a flux of emission radiation between a first flux level and a second different flux level in coordination with a cardiac cycle signal so that the flux is at the first flux level during a first cardiac motion phase having a first cardiac motion and is at the second flux level during a second cardiac motion phase having a second cardiac motion, wherein the first flux level is less than the second flux level, and wherein the first cardiac motion is greater than the second cardiac motion. An array of radiation sensitive of pixels is configured to detect radiation traversing the examination region and generate a signal indicative of the detected radiation. A reconstructor is configured to reconstruct the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

In yet another aspect, a computer readable storage medium is encoded with computer readable instructions, which, when executed by a processor, cause the processor to: modulate a flux of emission radiation between a first flux level and a second different flux level in coordination with a cardiac cycle signal so that the flux is at the first flux level during a first cardiac motion phase having a first cardiac motion and is at the second flux level during a second cardiac phase having a second cardiac motion, wherein the first flux level is less than the second flux level, and wherein the first cardiac motion greater than the second cardiac motion, receive projection data generated by a detector detecting the modulated emission radiation, and reconstruct the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
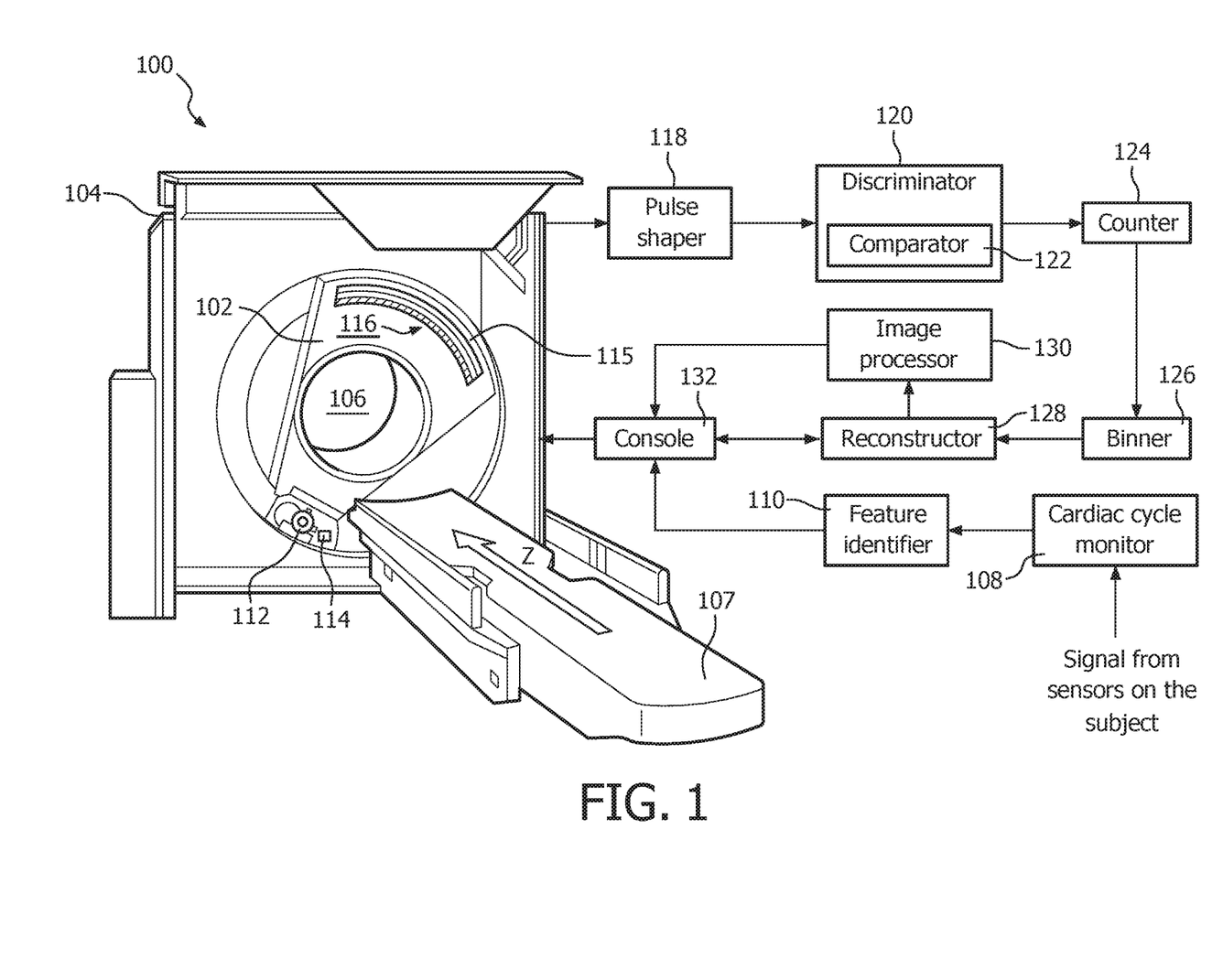
FIG. 1 schematically illustrates an example imaging system with an array of photon counting detector pixels.

FIG. 1 schematically illustrates an example imaging system 100, such as a computed tomography (CT) scanner. The imaging system 100 includes a rotating gantry 102 and a stationary gantry 104. The rotating gantry 102 is rotatably supported by the stationary gantry 104. The rotating gantry 102 is configured to rotate around an examination region 106 about a longitudinal or z-axis. The imaging system 100 further includes a subject support 107 that supports a subject or object in the examination region 106 before, during and/or after scanning. The subject support 107 can also be used to load and/or unload the subject or object into or from the examination region 106.

In the illustrated example, a cardiac cycle monitor 108 and a feature identifier 110 are employed with the example imaging system 100 for cardiac scans. In one instance, the cardiac cycle monitor 108 and/or the feature identifier 110 are part of the imaging system 100. In another instance, the cardiac cycle monitor 108 and/or the cardiac cycle feature identifier 110 are separate from the imaging system 100. The cardiac cycle monitor 108 receives electrical signals from sensors disposed on and/or near a subject and generates a cardiac cycle signal indicative of an electrical activity of the heart such as an electrocardiogram (ECG or EKG).

Figure 2:
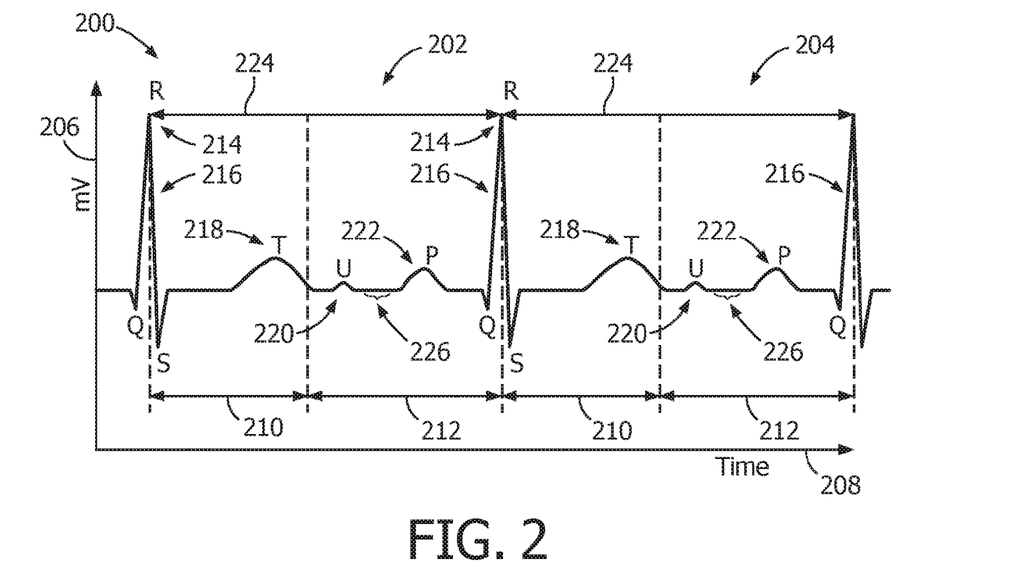
FIG. 2 illustrates an example of an ECG signal.

FIG. 2 illustrates an example of a sub-portion of an ECG signal 200 with two cardiac cycles 202 and 204. In FIG. 2, a first or y-axis 206 represents voltage in units of millivolts (mV), and a second or x-axis 208 represents time. Each of the cardiac cycles 202 and 204 includes a ventricular systolic period 210 and a ventricular diastolic period 212. Generally, the ventricular systolic period 210 begins shortly after an R peak 214 of a QRS complex 216 of the cardiac cycles 202 and 204, and ends near an end of a T wave 218. During the systolic period 210, the ventricular ventricles contract (the QRS complex 216) and then subsequently re-polarize (the T wave 218).

The ventricular diastolic period includes a U wave 220 (papillary muscle repolarization) and a P wave 222 (atrial contraction). During the ventricular diastolic period 212, the heart relaxes and the ventricles refill with circulating blood. An R-R interval 224 represents a time duration of a cardiac cycle relative to the R peaks 214 of the cardiac cycles 202 and 204. A region 226 corresponds to a region in which a motion of the heart is minimal relative to other regions of the cardiac cycle and has been referred to as a "quiet phase." Generally, such regions have been located at approximately 40%, 70%, etc. into the R-R interval 224.

With reference to FIGS. 1 and 2, the feature identifier 110 is configured to identify a predetermined feature of the cardiac cycle signal generated by the cardiac cycle monitor 108. For example, the feature identifier 110 is configured to identify a peak of a particular wave (e.g., the QRS complex 216, the T wave 218, the U wave 220, the P wave 222 and/or other wave). In one non-limiting instance, the feature identifier 110 is configured to identify the R peak 214. This can be achieved through a voltage level thresholding and/or other approach. Once identified, the feature identifier 110 generates a trigger signal that indicates the predetermined feature of the cardiac cycle was identified.

With reference to FIG. 1, the imaging system 100 further includes a radiation source 112, such as an x-ray tube, that is rotatably supported by the rotating gantry 102. The radiation source 112 rotates with the rotating gantry 102 around the examination region 106 and is configured to generate and emit radiation that traverses the examination region 106. The imaging system 100 further includes a radiation source controller 114. The radiation source controller 114 is configured to modulate a flux of the generated radiation. For example, the radiation controller 114 can selectively change a cathode heating current of the radiation source 112, apply a charge to inhibit electron flow of the radiation source 112, filter the emitted radiation, etc. to modulate the flux. In the illustrated example, the radiation source controller 114 modulates the flux based on a predetermined modulation pattern.

Figure 3:
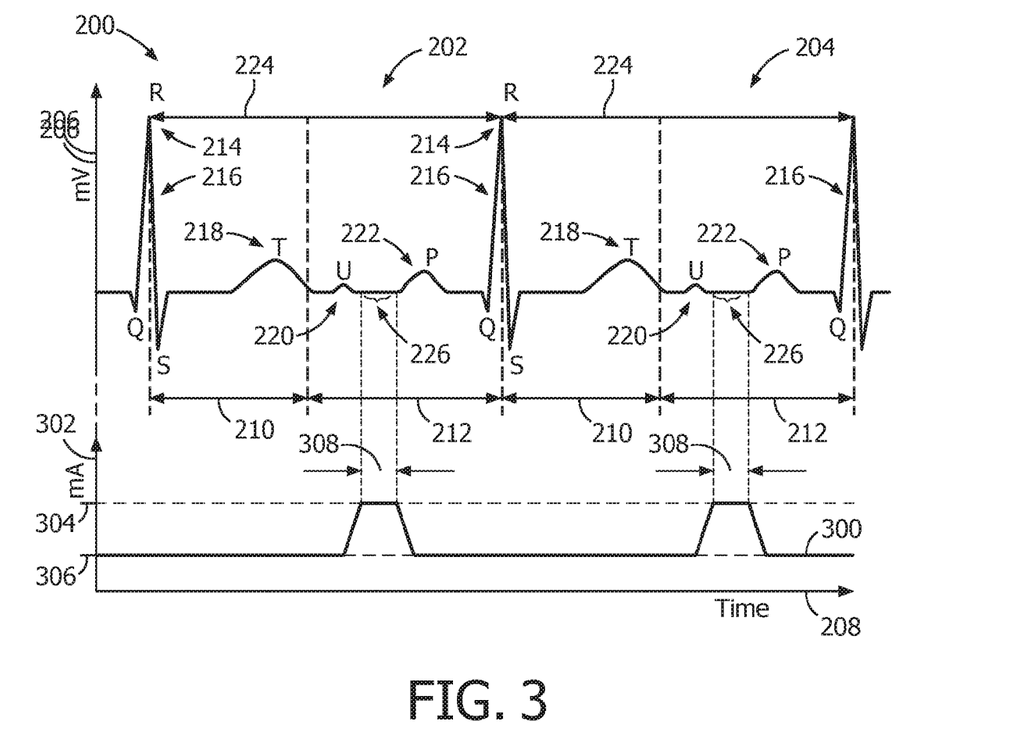
FIG. 3 illustrates an example flux modulation pattern in connection with the example ECG signal.

FIG. 3 show an example modulation pattern 300 in connection with the ECG signal 200. In FIG. 3, a first or y-axis 302 represents electrical current in units of milliamperes (mA). The illustrated modulation pattern 300 shares the x-(time) axis 208 with the ECG signal 200. In this example, the modulation pattern 300 switches the flux of the generated radiation between a higher flux level 304 and a lower (non-zero) flux level 306. Furthermore, the modulation pattern 300 switches the flux of the generated radiation to the higher flux level 304 for a time window 308 that corresponds to the quiet phase 226 and to the lower flux level 306 outside of the quiet phase 226. In other embodiments, the modulation pattern 300 can switch for a different and/or an additional phase(s), between more than two different flux levels, in a discrete and/or continuous manner, etc. In a variation, the modulation pattern may also include one or more regions where the tube current and hence the flux is zero. This can be achieved with a grid switching tube and/or a physical filter that can be positioned in and out of the beam path.

Returning to FIG. 1, the imaging system 100 further includes a one or two dimensional array 115 of radiation sensitive detector pixels 116. The pixels 116 are located opposite the radiation source 112, across the examination region 106, detect radiation traversing the examination region 106, and generate an electrical signal (projection data) indicative thereof. In the illustrated example, the pixels 116 include direct conversion photon counting detector pixels. With such pixels, the generated signal includes an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs or other direct conversion material.

The imaging system 100 further includes a pulse shaper 118 that processes the electrical signal output by the detector pixels 116 and generates a pulse such as voltage or other pulse indicative of the energy of the detected photon. In a variation, the electrical signal output by the detector pixels 116 is pre-processed (e.g., amplified, etc.), and the pulse shaper 118 processes the pre-processed signal. The imaging system 100 may further include an energy discriminator 120 that energy discriminates the pulse. In the illustrated example, the energy discriminator 120 includes at least one comparator 122, which compares the amplitude of the pulse with at least one energy threshold that corresponds to an energy of interest. The comparator 122 produces an output signal indicative of whether the energy of a detected photon is above or below the threshold.

The imaging system 100 further includes a counter 124 that increments (or decrements) a count value for each threshold. For instance, when the output of the comparator 122 for a particular threshold indicates that the amplitude of the pulse exceeds the corresponding threshold, the count value for that threshold is incremented. The imaging system 100 further includes a binner 126 that assigns the counted pulses to energy bins, which correspond to different energy ranges. For example, a bin may be defined for the energy range between two thresholds. With this example, the binner 126 assigns a photon resulting in a count for the lower threshold but not for higher threshold to the bin defined for the energy range between two thresholds.

The imaging system 100 further includes a reconstructor 128 that reconstructs the binned data using a spectral and/or a non-spectral algorithm and generates spectral and/or non-spectral volumetric image data. The reconstructor 128 can employ filtered backprojection, iterative, and/or other reconstruction algorithms. This includes weighted and non-weighted reconstruction algorithms. As described in greater detail below, an example weighted reconstruction algorithm weights the projection data to a greater degree for projection data acquired when the flux is at the higher flux level 304. In another example, the weighted reconstruction algorithm weights the projection data to a greater degree for projection data acquired when the flux is at the lower flux level 306.

Such algorithms are well-suited for cardiac studies using the modulation pattern 300 shown in FIG. 3 and/or other flux modulation pattern that control the flux so that it is at a high level during the quiet phase of the cardiac cycle. For example, the weighted reconstruction algorithm that weights the projection data to a greater degree for projection data acquired when the flux is at the higher flux level 304 for the quiet phase 226 can be used to generate volumetric image data of the heart, and the weighted reconstruction algorithm that weights the projection data to a greater degree for projection data acquired when the flux is at the lower flux level 306 for other phases can be used to generate volumetric image data of the lungs (and optionally the periphery of a subject).

This can be achieved as described in the following. Prior to a scan, a tube current modulation pattern is determined. For example, the pattern may be ramp the current up three hundred milliseconds (300 msec) after the last R-peak and reduce the current again another 300 msec later. This pattern presumes an approximately constant heartbeat of a certain length. For the reconstruction, an image is reconstructed at 70% of the cardiac cycle. The duration of the higher flux level 304 can be longer than the required gating window width for the reconstruction. If so, the weight need not be always high when the flux is at the higher flux level 304. However, the weight can always high when the flux is at the higher flux level 304.

In this manner, the volumetric image data of the heart will have suitable signal-to-noise ratio for diagnostic purposes. In addition, the volumetric image data of the lungs will not include artifact caused by the limited count rate of the photon counting detector pixels of the array of radiation sensitive of pixels 116. Furthermore, subject dose is reduced relative to scanning entirely at the higher level of flux 304.

The volumetric image data of the heart and the volumetric image data of the lungs can be visually displayed concurrently in different, overlapping, or a same display window of a display screen. Additionally, the volumetric image data of the heart and the volumetric image data of the lungs can be visually displayed alternatively. An image processor 130 can be used to combine the volumetric image data of the heart and the volumetric image data of the lungs to form a single volumetric image data set. For this, in one example, the heart or the lungs can be segmented and combined with the volumetric image data of the lungs or the volumetric image data of the heart.

The imaging system 100 further includes a computing system that serves as an operator console 132 and includes an output device such as a display and an input device such as a keyboard, mouse, and/or the like. Software resident on the console 132 allows a user to control an operation of the system 100. For example, the console 132 can be used to identify an imaging protocol (e.g., a cardiac imaging protocol with flux modulation and weighted reconstruction), initiate scanning, and the control the radiation source controller 114 and reconstructor 128 based on the identified imaging protocol to modulate the flux and employ particular reconstruction algorithms.

It is to be appreciated that the cardiac monitor 108, the feature identifier 110, the pulse shaper 118, the discriminator 120, the comparator 122, the counter 124, the binner 126, the reconstructor 128, the image processor 130, and the console 132 can be implemented via electrical circuitry and/or software/firmware. For instance, the console 132 includes one or more processors (e.g., a central processing unit, a microprocessor, etc.), and computer readable medium (which excludes transitory and includes physical memory) encoded with computer executable instructions, which, when executed by the one or more processors, causes the one or more processors to perform one or more of the functions described herein.

As briefly described above, the reconstructor 128 can employ a weighted reconstruction algorithm. The following describes examples of weighted reconstruction algorithms. Generally, a width of each reconstruction window is determined by a completeness condition of the reconstruction such that every voxel is radiated by the source for at least one hundred and eighty degrees (180°) plus fan angle (or for 180° after fan beam to parallel cone beam rebinning).

Figure 4:
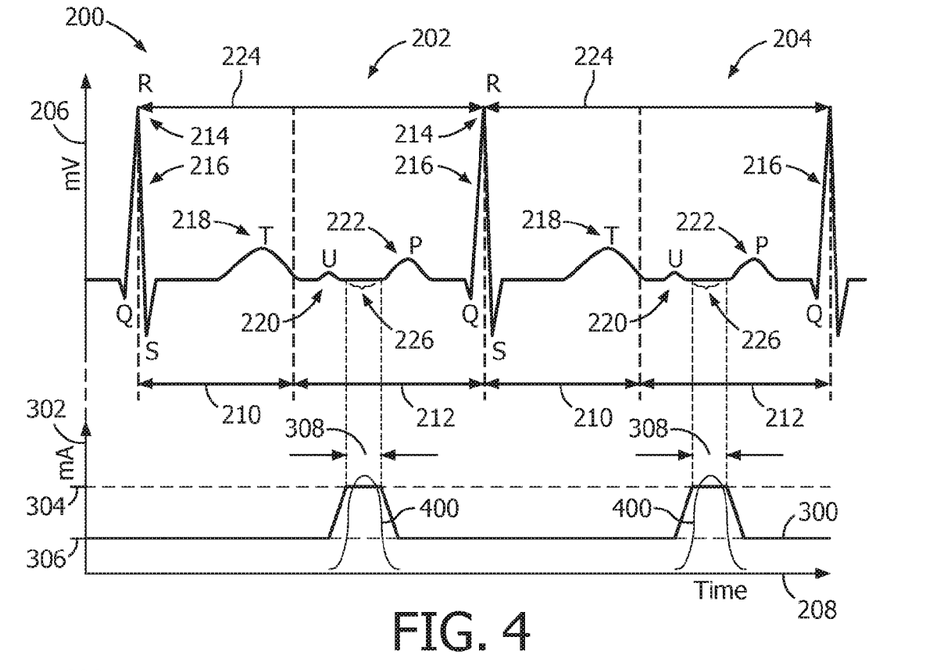
FIG. 4 illustrates an example cardiac reconstruction window in connection with the example ECG signal.

FIG. 4 shows an example reconstruction algorithm with a reconstruction window 400 in connection with the ECG 200 and the modulation pattern 300. In this example, the reconstruction window 400 is a cardiac reconstruction window for the heart. In this example, the cardiac reconstruction window 400 corresponds to the quiet phase 226 and lies within a time period in which the radiation source current is modulated at the higher flux level 304. In other embodiments, the cardiac reconstruction window 400 can be narrower or wider, including covering time when the radiation source current is modulated at the lower flux level 306.

Figure 5:
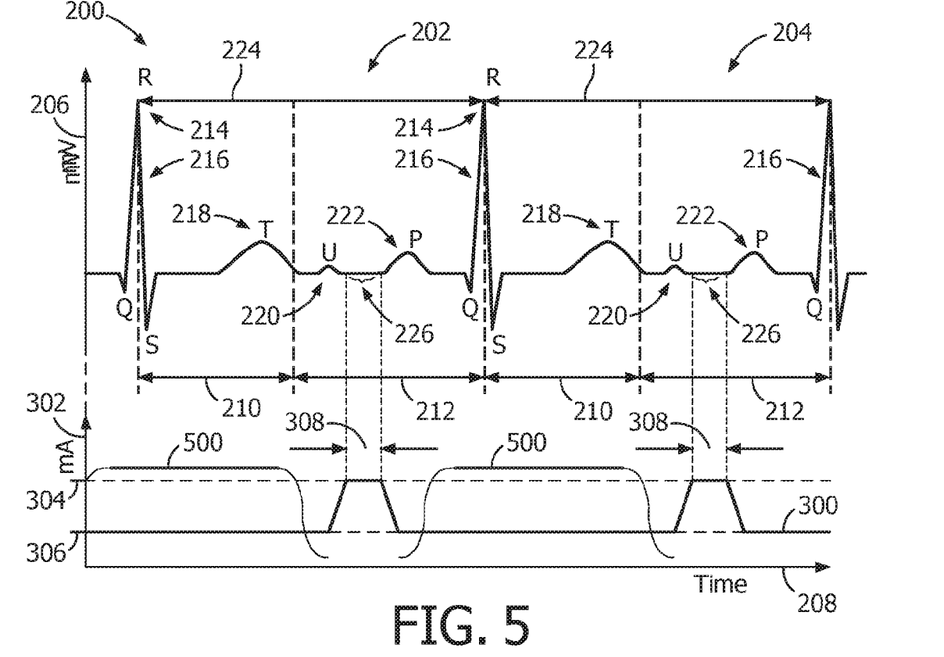
FIG. 5 illustrates an example lung reconstruction window in connection with the example ECG signal.
Figure 6:
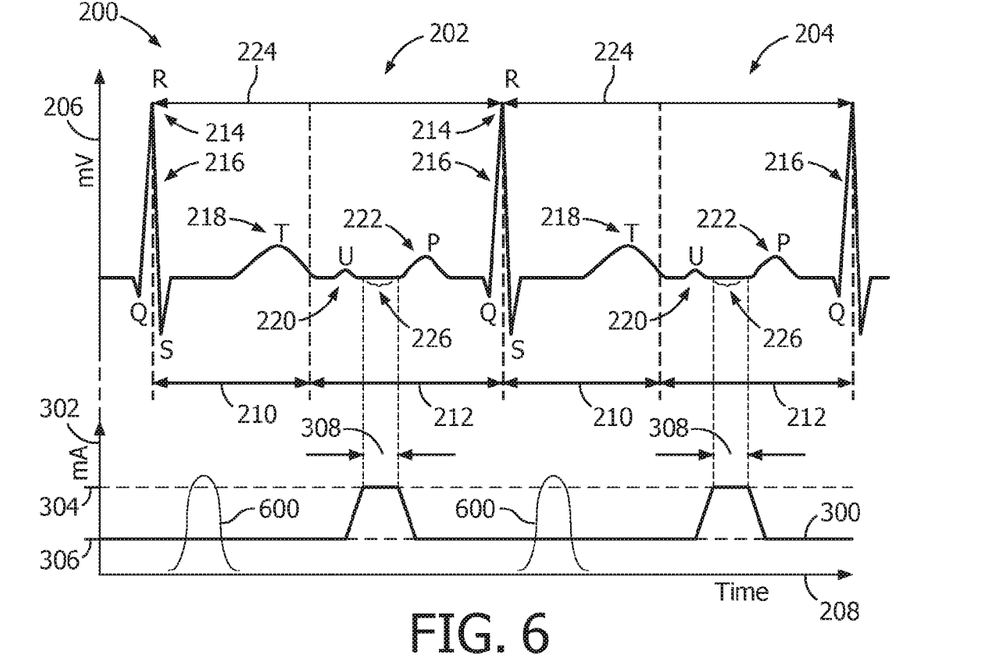
FIG. 6 illustrates another example lung reconstruction window in connection with the example ECG signal.
Figure 7:
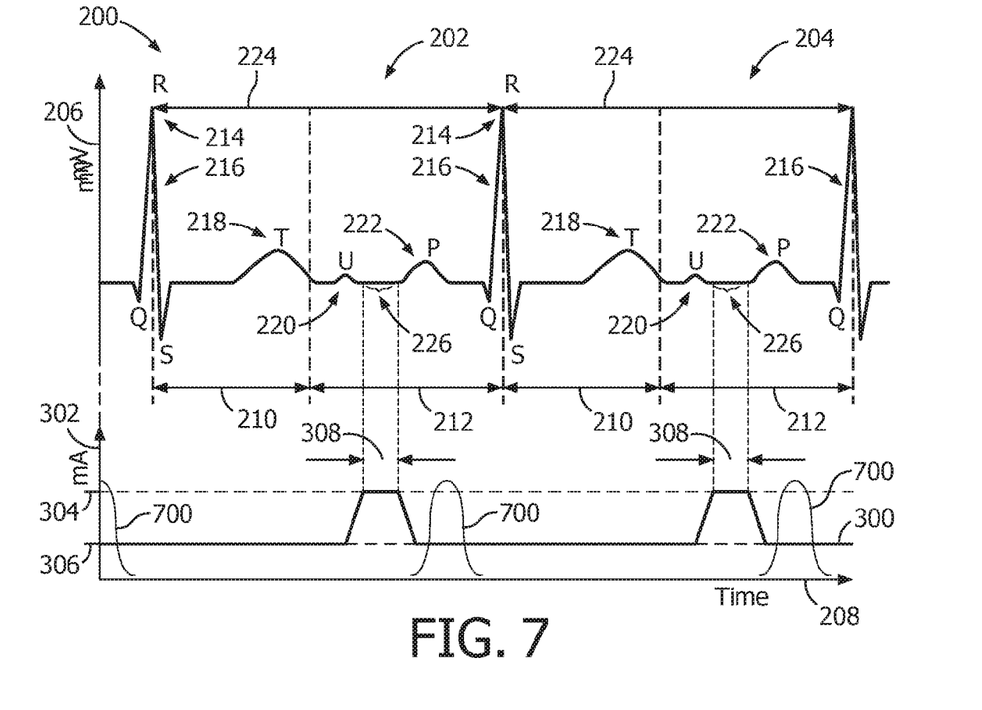
FIG. 7 illustrates another example lung reconstruction window in connection with the example ECG signal.

FIGS. 5, 6 and 7 respectively show example reconstruction algorithms with reconstruction windows 500, 600 and 700 in connection with the ECG 200 and the modulation pattern 300. In these figures, the reconstruction windows 500, 600 and 700 are respiratory reconstruction windows for the lungs.

In FIG. 5, the respiratory reconstruction window 500 covers the entire time the radiation source current is modulated at the lower flux level 306. In FIG. 6, the respiratory reconstruction window 600 covers only part of the time the radiation source current is modulated at the lower flux level 306. In FIG. 7, the respiratory reconstruction window 700 is proximate to the cardiac reconstruction window 400 (FIG. 4) but only where the radiation source current is modulated at the lower flux level 306.

As a consequence, with the respiratory reconstruction window 700 of FIG. 7, the motion states of the cardiac and the lung images will have minimal difference. The respiratory reconstruction window 700 may be positioned either prior to or after (as shown in FIG. 7) the cardiac reconstruction window 400. In a variation, the respiratory reconstruction window 700 could also be split up in a part prior and a part post the cardiac reconstruction window 400.

A non-limiting example of a non-iterative reconstruction is described in Koken, "Aperture weighted cardiac reconstruction for cone-beam CT," Phys. Med. Biol. 51 (2006) 3433-3448. A non-limiting example of an iterative reconstruction is described in Nielsen, "Cardiac cone-beam CT volume reconstruction using ART," Med. Phys. 32 (4) (2005) 851-860. From Koken, a suitable reconstruction can be formulated as shown in EQUATION 1:

$$f(\vec{x}) = \frac{1}{2\pi} \sum_{l=1}^{N_\omega(\vec{x})} \int_{l_l(\vec{x})} \omega_{all}(\phi, \vec{x}) P_4(\phi, u(\phi, \vec{x}), h(\phi, \vec{x})) d\phi, \quad \text{EQUATION 1}$$

where $(\vec{x})$ represents an object point, $f(\vec{x})$ represents an object function, $l$ and $N_\omega(\vec{x})$ represents indices, $\omega_{all}(\phi, \vec{x})$ represents a weighting function, $P_4(\phi, u, h)$ represents preprocessed projection data, $\phi$ represents an angle of parallel lines projected onto an xy-plane, and $\mu(\phi, \vec{x})$ and $h(\phi, \vec{x})$, represent projected detector coordinates of the object point.

For cardiac reconstruction, $$\omega_{all}(\phi, \vec{x}) = \frac{\omega_c(\phi)\omega_{ap}(\phi, \vec{x})}{\Sigma_n \omega_c(\phi + n\pi)\omega_{ap}(\phi + n\pi, \vec{x})},$$

where $\omega_c$ represents a cardiac weight, $\omega_{ap}$ represents an aperture weight, $\phi + n\pi \in I_l(\vec{x})$, and $l=1, \ldots, N_\omega(\vec{x})$. For lung reconstruction, $$\omega_{all}(\phi, \vec{x}) = \frac{\omega_l(\phi)\omega_{ap}(\phi, \vec{x})}{\Sigma_n \omega_l(\phi + n\pi)\omega_{ap}(\phi + n\pi, \vec{x})},$$

where $\omega_l(\phi)=1$ for all $\{\phi | I(\phi)=I_{low}\}$ and 0 otherwise.

In another embodiment, $\omega_l(\phi)=1$ for all projections in which the X-ray flux to the detector does not exceed a predetermined threshold indicative of the count rate limit of the detector, and $\omega_l(\phi)=0$ for all projections in which the X-ray flux to the detector does exceed the predetermined threshold indicative of the count rate limit of the detector. This embodiment is well suited for a configuration in which excessive flux levels can be detected within the detector itself through hardware, software, and/or otherwise.

In other embodiments, $\omega_l(\phi)$ includes $\cos^2$ smoothing on the boundaries, a minimum temporal distance to cardiac phase points, or a temporal width to guarantee one hundred and eighty degrees plus a fan angle of data but not more. In another instance, $\omega_l(\phi, u, h)=\omega_l(\phi) \cdot w_l^d(\phi, u, h)$, where $w_l^d(\phi, u, h)$ is 1 for all $\{(\phi, u, h)|I^{det}(\phi, u, h)<I^{sat}\}$ and 0 otherwise. In this instance, $I^{sat}$ is the intensity at which the detector is saturated and $\omega_l(\phi)$ is a weighting function as described herein.

Figure 8:
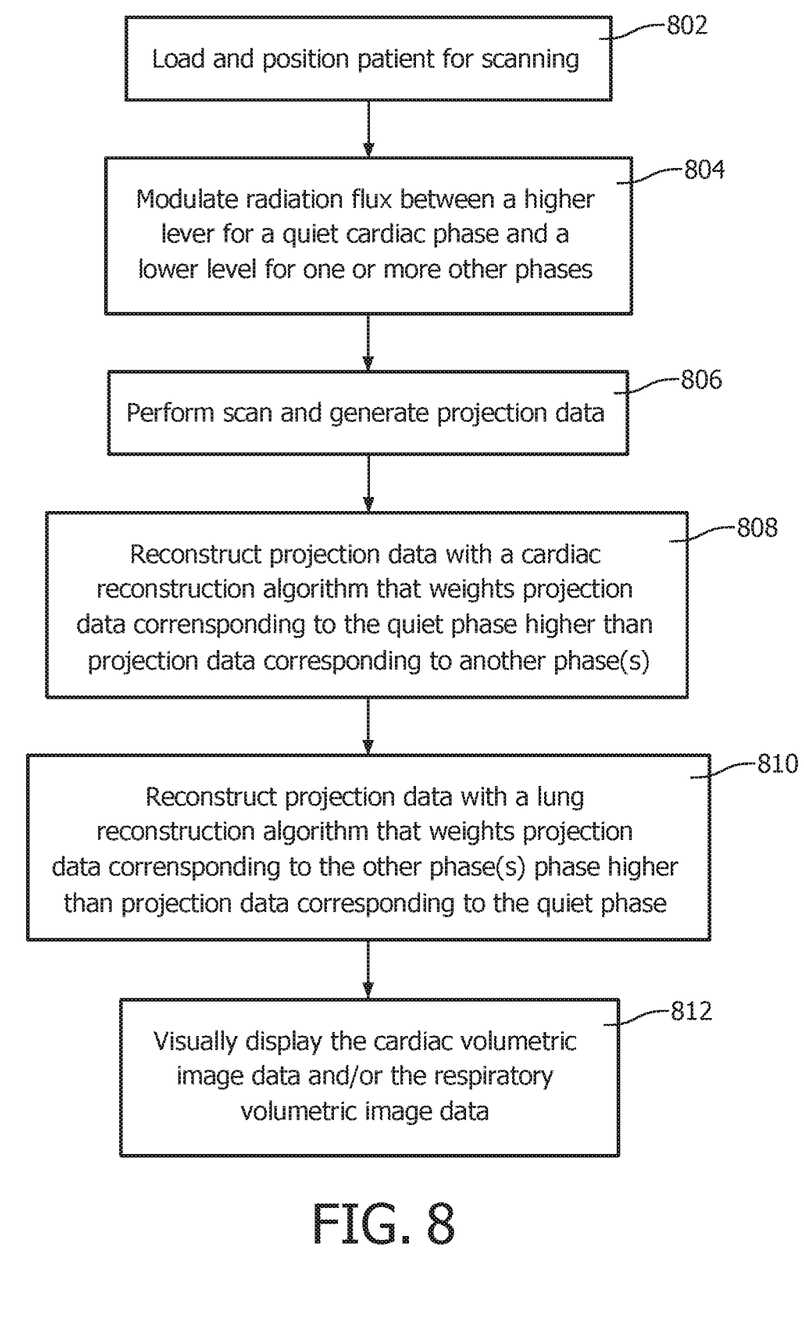
FIG. 8 illustrates a method in accordance with an embodiment herein.

FIG. 8 illustrates a method in accordance with an embodiment described herein.

It is to be appreciated that the ordering of the below acts is for explanatory purposes and not limiting. As such, other orderings are also contemplated herein. In addition, one or more of the acts may be omitted and/or one or more other acts may be included.

At 802, a patient is loaded onto the subject support of an imaging system with photon counting detector pixels and positioned with respect to an imaging region for scanning.

At 804, a radiation emission flux is modulated between at least a first flux level and a second flux level, where the first flux level is higher than the second flux level, and the modulation is in coordination with a quiet phase of a cardiac cycle of the patient so that the radiation emission flux during the quiet phase is the higher flux.

At 806, a scan is performed, generating projection data. It is to be appreciated that the scan can be a gated reconstruction for a circular, a helical, step and shoot (e.g., axial), and/or other scans.

At 808, the projection data is reconstructed with a cardiac weighted reconstruction algorithm, which weights a first portion of the projection data corresponding to the quiet phase higher than a second portion of the projection data corresponding to one or more phases outside of the quiet phase, generating cardiac volumetric image data.

At 810, the projection data is reconstructed with a lung weighted reconstruction algorithm, which weights the second portion of the projection data corresponding to the one or more phases outside of the quiet phase higher than the first portion of the projection data corresponding to the quiet phase higher, generating respiratory volumetric image data.

At 812, the cardiac volumetric image data and the respiratory volumetric image data are displayed, as discussed herein and/or otherwise.

At least a portion of the method discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
    modulating a flux of emission radiation between a first flux level and a second different flux level in coordination with a cardiac cycle signal so that the flux is at the first flux level during a first cardiac motion phase having a first cardiac motion and is at the second flux level during a second cardiac motion phase having a second cardiac motion, wherein the first flux level is less than the second flux level, and wherein the first cardiac motion is greater than the second cardiac motion;
    detecting the modulated emission radiation;
    producing projection data indicative of the detected modulated emission radiation; and
    reconstructing the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

2. The method of claim 1, wherein the first weight has a non-zero value and the second weight has a value of zero.

3. The method of claim 2, further comprising:
reconstructing the projection data with a second reconstruction window, which applies a third weight to the second sub-set of the projection data that corresponds to the second cardiac motion phase and the higher second flux level and a fourth weight to the first sub-set of the projection data that corresponds to the first cardiac motion phase and the lower first flux level, wherein the third weight is greater than the fourth weight, to generate second volumetric image data.

4. The method of claim 3, further comprising:
applying the first weight to projection data corresponding to one or more cardiac motion phases that are adjacent to the second cardiac motion phase.

5. The method of claim 4, wherein the one or more cardiac motion phases occurs before the second cardiac motion phase.

6. The method of claim 4, wherein the one or more cardiac motion phases occurs after the second cardiac motion phase.

7. The method of claim 4, wherein a first sub-set of the one or more cardiac motion phases occurs before the second cardiac motion phase and a second sub-set of the one or more cardiac motion phases occurs after the second cardiac motion phase.

8. The method of claim 1, further comprising:
applying the first weight to an entire set of projection data corresponding to the first cardiac motion phase.

9. The method of claim 8, further comprising:
reconstructing the projection data with a second reconstruction window, which applies a third weight to the second sub-set of the projection data that corresponds to the second cardiac motion phase and the higher second flux level and a fourth weight to the first sub-set of the projection data that corresponds to the first cardiac motion phase and the lower first flux level, wherein the third weight is greater than the fourth weight, to generate second volumetric image data.

10. The method of claim 1, further comprising:
applying the first weight to a first sub-set of the projection data corresponding to the first cardiac motion phases.

11. The method of claim 1, further comprising:
applying a first weight, that is equal to one, to the projection data in response to the X-ray flux irradiating the detector not exceeding a predetermined threshold indicative of the count rate limit of the detector; and
applying a second weight, that is equal to zero, to the projection data in response to the X-ray flux irradiating the detector exceeding the predetermined threshold indicative of the count rate limit of the detector.

12. An imaging system, comprising:
a radiation source configured to rotate about an examination region and emit radiation that traverses the examination region;
a radiation source controller configured to control the radiation source to modulate a flux of emission radiation between a first flux level and a second different flux level in coordination with a cardiac cycle signal so that the flux is at the first flux level during a first cardiac motion phase having a first cardiac motion and is at the second flux level during a second cardiac motion phase having a second cardiac motion, wherein the first flux level is less than the second flux level, and wherein the first cardiac motion is greater than the second cardiac motion; and
an array of radiation sensitive of pixels configured to detect radiation traversing the examination region and generate a signal indicative of the detected radiation; and
a reconstructor configured to reconstruct the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

13. The imaging system of claim 12, wherein the first weight has a non-zero value and the second weight is zero.

14. The imaging system of claim 13, wherein the reconstructor is further configured to reconstruct the projection data with a second reconstruction window, which applies a third weight to the second sub-set of the projection data that corresponds to the second cardiac motion phase and the higher second flux level and a fourth weight to the first sub-set of the projection data that corresponds to the first cardiac motion phase and the lower first flux level, wherein the third weight is greater than the fourth weight, to generate second volumetric image data.

15. The imaging system of claim 13, wherein the reconstructor is further configured to reconstruct the projection data with a second reconstruction window, which applies a third weight to the second sub-set of the projection data that corresponds to the second cardiac motion phase and a fourth weight to the first sub-set of the projection data that corresponds to the first cardiac motion phase, wherein the third weight is greater than the fourth weight, to generate second volumetric image data.

16. The imaging system of claim 15, wherein the first weight is applied to projection data corresponding to one or more cardiac motion phases that are adjacent to the second cardiac motion phase.

17. The imaging system of claim 16, wherein the one or more cardiac motion phases occurs at least one of before or after the second cardiac motion phase.

18. The imaging system of claim 16, wherein a first sub-set of the one or more cardiac motion phases occurs before the first cardiac motion phase and a second sub-set of the one or more cardiac motion phases occurs after the first cardiac motion phase.

19. The imaging system of claim 12, wherein the first weight is applied to an entire set of projection data corresponding to the first cardiac motion phase.

20. The imaging system of claim 12, wherein the first weight is applied to a first sub-set of the projection data corresponding to the first cardiac motion phase.

21. A computer readable storage medium encoded with computer readable instructions, which, when executed by a processor, causes the processor to:
modulate a flux of emission radiation between a first flux level and a second different flux level in coordination with a cardiac cycle signal so that the flux is at the first flux level during a first cardiac motion phase having a first cardiac motion and is at the second flux level during a second cardiac phase having a second cardiac motion, wherein the first flux level is less than the second flux level, and wherein the first cardiac motion greater than the second cardiac motion;

receive projection data generated by a detector detecting the modulated emission radiation; and reconstruct the projection data with a first reconstruction window, which applies a first weight to a first sub-set of the projection data that corresponds to the first cardiac motion phase and the lower first flux level and a second different weight to a second sub-set of the projection data that corresponds to the second cardiac motion phase and the higher second flux level, to generate first volumetric image data, wherein the first weight is greater than the second weight.

* * * * *